US008761854B2

(12) United States Patent
Price et al.

(10) Patent No.: US 8,761,854 B2
(45) Date of Patent: *Jun. 24, 2014

(54) METHOD FOR RESPIRATION RATE AND BLOOD PRESSURE ALARM MANAGEMENT

(71) Applicant: Covidien LP, Mansfield, MA (US)

(72) Inventors: Thomas Price, Denver, CO (US); Ron J. Kadlec, Longmont, CO (US)

(73) Assignee: Coviden LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/937,388

(22) Filed: Jul. 9, 2013

(65) Prior Publication Data
US 2013/0296675 A1 Nov. 7, 2013

Related U.S. Application Data

(63) Continuation of application No. 12/771,859, filed on Apr. 30, 2010, now Pat. No. 8,498,683.

(51) Int. Cl.
A61B 5/00 (2006.01)

(52) U.S. Cl.
USPC .......................................................... 600/324

(58) Field of Classification Search
USPC ........................................ 600/484, 324, 326
See application file for complete search history.

(56) References Cited

U.S. PATENT DOCUMENTS

| 4,603,700 | A | 8/1986 | Nichols et al. |
| 4,776,339 | A | 10/1988 | Schreiber |
| 5,253,645 | A | 10/1993 | Friedman et al. |
| 5,309,908 | A | 5/1994 | Friedman et al. |
| 5,368,026 | A | 11/1994 | Swedlow et al. |
| 5,517,988 | A | 5/1996 | Gerhard |
| 5,662,106 | A | 9/1997 | Swedlow et al. |

(Continued)

FOREIGN PATENT DOCUMENTS

| JP | 27167185 | 7/2007 |
| JP | 27330708 | 12/2007 |

(Continued)

OTHER PUBLICATIONS

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

(Continued)

Primary Examiner — Clayton E Laballe
Assistant Examiner — Leon W. Rhodes
(74) Attorney, Agent, or Firm — Fletcher Yoder PC

(57) ABSTRACT

Embodiments of the present disclosure relate to display features that facilitate observation of monitored physiological data. According to certain embodiments, a monitoring system may include a monitor capable of receiving data related to the physiological parameters and storing data related to the parameters. The monitor may include a microprocessor configured to determine a blood pressure baseline from the data and to establish an alarm sensitivity for blood pressure based on the blood pressure baseline. The alarm sensitivity may comprise a first tier, a second tier, a third tier, and a fourth tier, and each tier may correspond to a blood pressure range. The alarm sensitivity may relate to an acceptable percent shift of the blood pressure from the blood pressure baseline, and the acceptable percent shift for at least one of the tiers is different from the acceptable percent shift of another one of the tiers.

20 Claims, 11 Drawing Sheets

(56) References Cited

U.S. PATENT DOCUMENTS

| | | |
|---|---|---|
| 5,807,246 A | 9/1998 | Sakaguchi et al. |
| 5,830,135 A | 11/1998 | Bosque et al. |
| 5,846,190 A | 12/1998 | Woehrle |
| 5,865,736 A | 2/1999 | Baker et al. |
| 5,920,263 A | 7/1999 | Huttenhoff et al. |
| 6,398,727 B1 | 6/2002 | Bui et al. |
| 6,415,166 B1 | 7/2002 | van Hoy et al. |
| 6,579,242 B2 | 6/2003 | Bui et al. |
| 6,606,511 B1 | 8/2003 | Ali et al. |
| 6,684,090 B2 | 1/2004 | Ali et al. |
| 6,754,516 B2 | 6/2004 | Mannheimer |
| 6,801,802 B2 | 10/2004 | Sitzman et al. |
| 6,822,564 B2 | 11/2004 | Al-Ali |
| 6,830,549 B2 | 12/2004 | Bui et al. |
| 6,930,608 B2 | 8/2005 | Grajales et al. |
| 6,963,767 B2 | 11/2005 | Rantala et al. |
| 6,985,762 B2 | 1/2006 | Brashears et al. |
| 6,996,427 B2 | 2/2006 | Ali et al. |
| 7,024,233 B2 | 4/2006 | Ali et al. |
| 7,040,315 B1 | 5/2006 | Stromberg |
| 7,161,484 B2 | 1/2007 | Tsoukalis |
| 7,220,220 B2 | 5/2007 | Stubbs et al. |
| 7,268,672 B2 | 9/2007 | King |
| 7,294,112 B1 | 11/2007 | Dunlop |
| 7,387,607 B2 | 6/2008 | Holt et al. |
| 8,498,683 B2 * | 7/2013 | Price et al. .................. 600/324 |
| 2002/0190863 A1 | 12/2002 | Lynn |
| 2002/0198442 A1 | 12/2002 | Rantala et al. |
| 2004/0133087 A1 | 7/2004 | Ali et al. |
| 2004/0215069 A1 | 10/2004 | Mannheimer |
| 2005/0017864 A1 | 1/2005 | Tsoukalis |
| 2006/0161389 A1 | 7/2006 | Weber et al. |
| 2006/0195025 A1 | 8/2006 | Ali et al. |
| 2006/0266355 A1 | 11/2006 | Misholi |
| 2007/0100213 A1 | 5/2007 | Dossas et al. |
| 2007/0156450 A1 | 7/2007 | Roehm et al. |
| 2007/0282177 A1 | 12/2007 | Pitz |
| 2008/0071155 A1 | 3/2008 | Kiani |
| 2008/0091092 A1 | 4/2008 | Al-Ali |
| 2008/0183058 A1 | 7/2008 | Mannheimer |
| 2008/0191866 A1 | 8/2008 | Falck et al. |
| 2008/0221418 A1 | 9/2008 | Al-Ali et al. |
| 2008/0228045 A1 | 9/2008 | Gao et al. |
| 2008/0228052 A1 | 9/2008 | Al-Ali |
| 2008/0275349 A1 | 11/2008 | Halperin et al. |
| 2008/0316488 A1 | 12/2008 | Mao et al. |
| 2010/0317986 A1 | 12/2010 | Colman et al. |

FOREIGN PATENT DOCUMENTS

| | | |
|---|---|---|
| WO | 9843071 | 10/1998 |
| WO | 2004075746 | 9/2004 |
| WO | 2005020120 | 3/2005 |

OTHER PUBLICATIONS

Belal, Suliman Yousef, et al.; "A fuzzy system for detecting distorted plethysmogram pulses in neonates and paediatric patients," Physiol. Meas., vol. 22, pp. 397-412 (2001).

Lutter, Norbert O., et al.; "False Alarm Rates of Three Third-Generation Pulse Oximeters in PACU, ICU and IABP Patients," Anesth Analg, vol. 94, pp. S69-S75 (2002).

* cited by examiner

METHOD FOR RESPIRATION RATE AND BLOOD PRESSURE ALARM MANAGEMENT

CROSS-REFERENCE TO RELATED APPLICATIONS

This application is a continuation of U.S. application Ser. No. 12/771,859, filed Apr. 30, 2010, entitled "Method for Respiration Rate and Blood Pressure Alarm Management."

BACKGROUND

The present disclosure relates generally to user-interface applications for patient monitoring devices. In particular, present embodiments relate to display features that facilitate observation of monitored physiological data with patient monitoring instruments.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Patient monitors include medical devices that facilitate measurement and observation of patient physiological data. A typical patient monitor cooperates with a sensor to detect and display a patient's vital signs (e.g., temperature, pulse rate, or respiratory rate) and/or other physiological measurements (e.g., water content of tissue, blood oxygen level, or blood pressure) for observation by a user (e.g., clinician). For example, pulse oximeters are generally utilized with related sensors to detect and monitor a patient's functional oxygen saturation of arterial hemoglobin (i.e., $SpO_2$) and pulse rate. Other types of patient monitors may be utilized to detect and monitor other physiological parameters. The use of patient monitors may improve patient care by facilitating supervision of a patient without continuous attendance by a human observer (e.g., a nurse or physician).

A patient monitor may include a screen that displays information relating to operation and use of the patient monitor. A typical patient monitor screen may display patient data for further interpretation by a caregiver. Such display information may include indications that relate to a patient's physiological conditions. In addition, a patient monitor may also be capable of generating alarms related to a patient's condition (e.g., changes in a physiological parameter). These patient-related alarms may alert a caregiver to conditions that may benefit from medical intervention. However, it may be desirable to manage the number of alarms to avoid alarms for minor, transient events and to convey the information to the caregiver about the patient's condition so that the information may be interpreted quickly if a more serious event occurs.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Different patients may exhibit different normal ranges of physiological characteristic values. Factors such as age, weight, height, diagnosis, and a patient's use of certain medications may affect the patient's normal ranges of physiological parameters. For example, for an adult, normal blood pressure may be 120 mmHg/80 mmHg (systolic/diastolic). In contrast, for a neonate, normal blood pressure may be 64 mmHg/41 mmHg. Accordingly, to trigger alarms it may be desirable to set different low and/or high thresholds for particular parameters based on the patient being monitored. In addition, simply monitoring a patient's physiological parameters may result in excessive alarms if a parameter repeatedly exceeds a threshold only momentarily. Accordingly, an alarm management method may be employed to reduce nuisance alarms on patient monitors. Also, numerous alarm systems monitoring different physiological parameters may be interrelated. Accordingly, an alarm management method may be employed to prioritize the alarm systems based on the particular parameters monitored.

Figure 1:
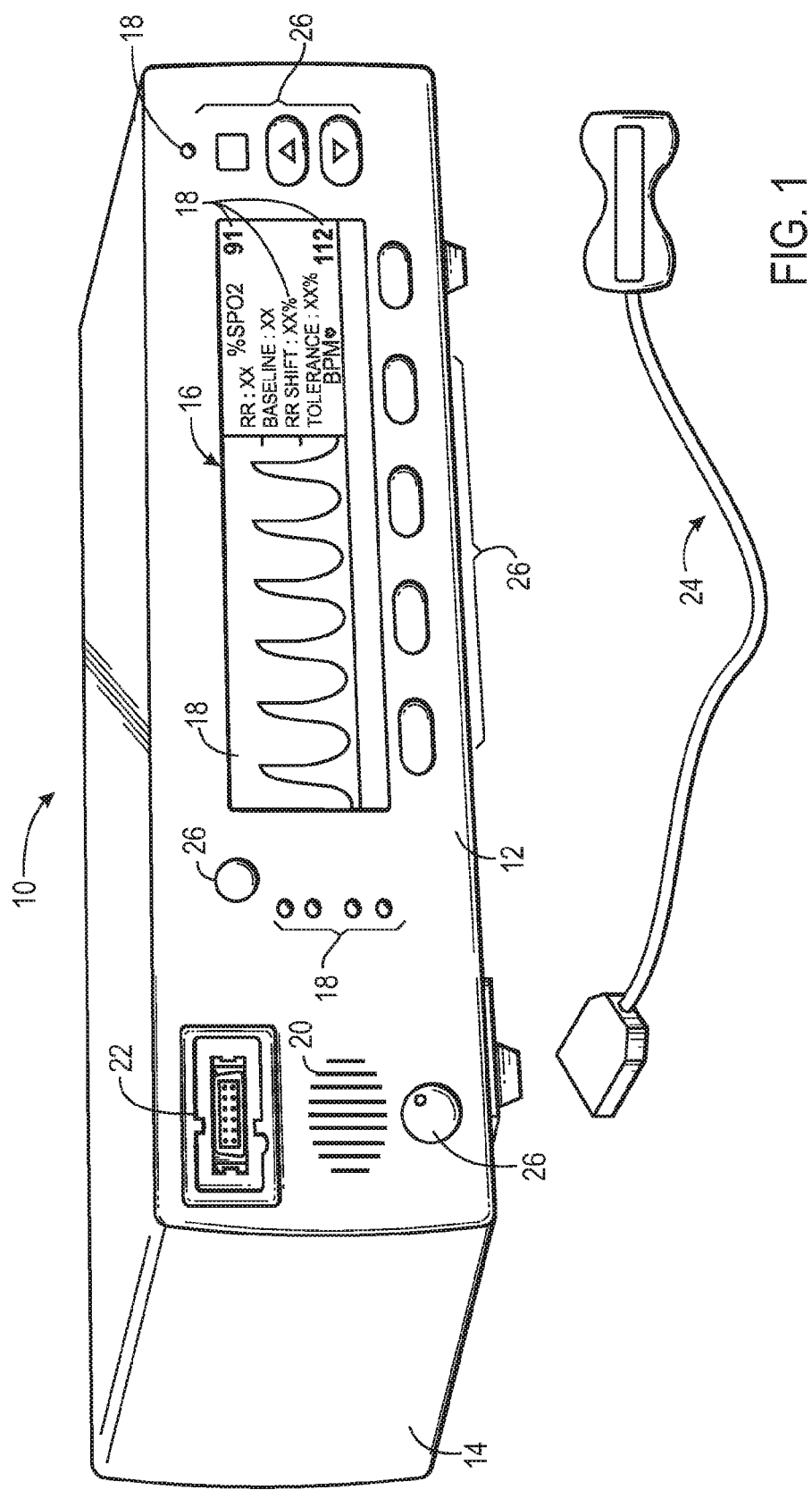
FIG. 1 is a perspective view of an embodiment of a patient monitor.

FIG. 1 is a perspective view of an example of a patient monitor 10 in accordance with an embodiment of the present disclosure. For example, the patient monitor 10 may be a pulse oximeter, such as those available from Nellcor Puritan Bennett LLC of Boulder, Colo. As illustrated, the patient monitor 10 is a pulse oximeter that is configured to detect and monitor blood oxygen saturation levels, pulse rate, and so forth. It should be noted that while the illustrated embodiment includes a pulse oximeter, other embodiments may include different types of patient monitors 10. For example, the patient monitor 10 may be representative of a vital signs monitor, a critical care monitor, an obstetrical care monitor, or the like.

The illustrated patient monitor 10 includes a front panel 12 coupled to a body 14 of the monitor 10. The front panel 12 includes a display screen 16 and various indicators 18 (e.g., indicator lights and display screen graphics) that facilitate operation of the monitor 10 and observation of a patient's physiological metrics (e.g., pulse rate). Some of the indicators 18 are specifically provided to facilitate monitoring of a patient's physiological parameters. For example, the indicators 18 may include representations of the most recently measured values for $SpO_2$, pulse rate, index values, and/or pulse amplitude. In some embodiments, the indicators 18 may include an indicator related to respiration rate. For example, the indicator 18 may be a respiration rate indicator that provides an indication related to shifts in respiration rate. Other indicators 18 may be specifically provided to facilitate operation of the monitor 10. For example, the indicators 18 may include an A/C power indicator, a low battery indicator, an alarm silence indicator, a mode indicator, and so forth. The front panel 12 may also include a speaker 20 for emitting audible indications (e.g., alarms), a sensor port 22 for coupling with a sensor 24 (e.g., a temperature sensor, a pulse oximeter sensor) and other monitor features.

Additionally, the front panel 12 may include various control inputs 26 (e.g., buttons and switches) to facilitate management and operation of the monitor 10. For example, the front panel 12 may include function keys (e.g., keys with varying functions), a power switch, adjustment buttons, an alarm silence button, and so forth. It should be noted that in other embodiments, the indicators 18 and control inputs 26 may be arranged on different parts of the monitor 10. In other words, the indicators 18 and control inputs 26 need not be located on the front panel 12. Indeed, in some embodiments, control inputs 26 are virtual representations in a display or actual components disposed on separate devices.

Figure 2:
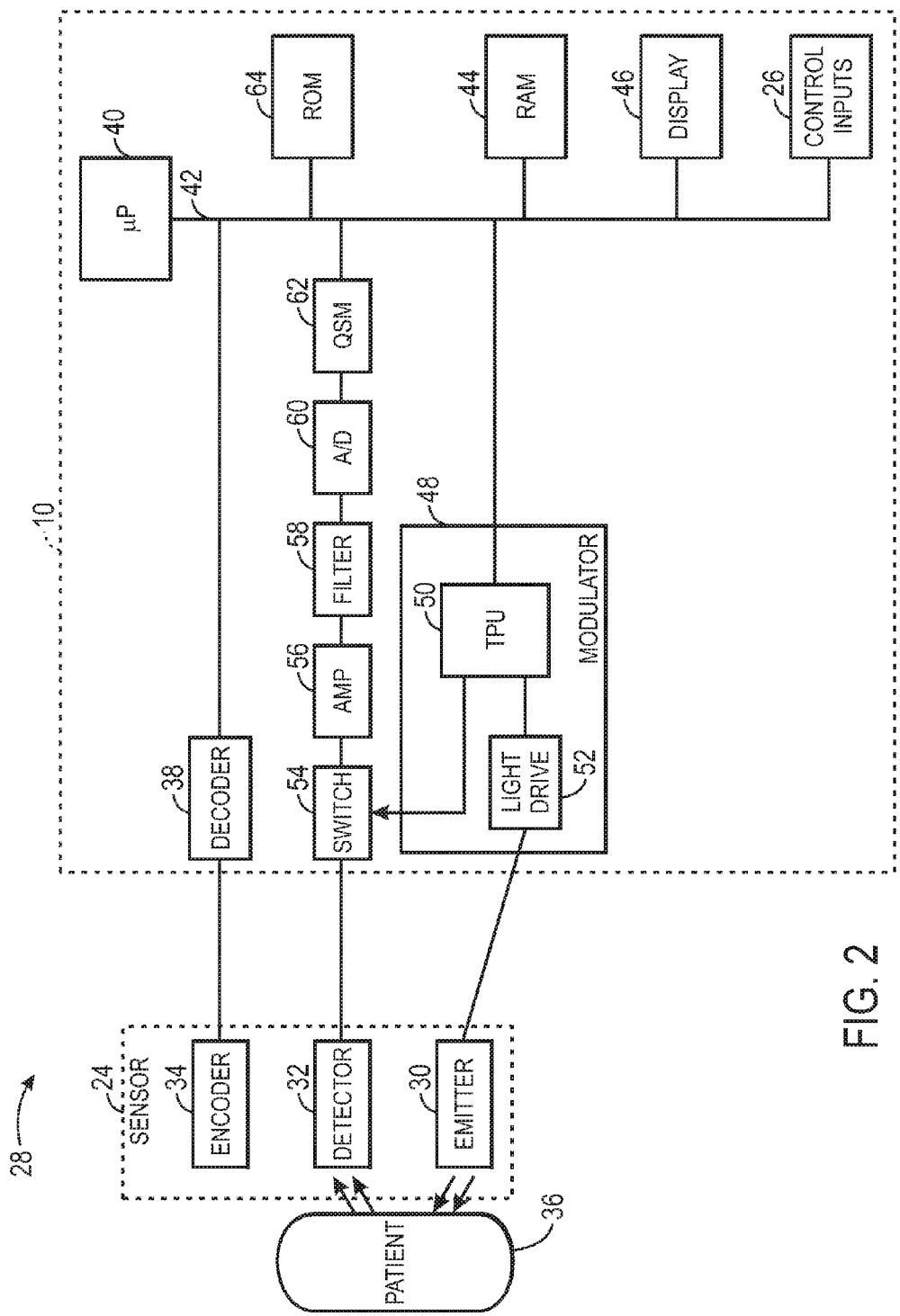
FIG. 2 is a simplified block diagram of an embodiment of a patient monitoring system.

Turning to FIG. 2, a simplified block diagram of a patient monitoring system 28 is illustrated in accordance with an embodiment. Specifically, certain components of the sensor 24 and the monitor 10 are illustrated in FIG. 2. The sensor 24 may include an emitter 30, a detector 32, and an encoder 34. The emitter 30 may receive modulated drive signals from the monitor 10, and may activate and deactivate a light emitting device at certain intervals. For example, the monitor 10 may activate and deactivate components that emit light of different wavelengths, such that light of a different wavelength is alternately emitted.

The emitter 30 may be capable of emitting one or more wavelengths of light, e.g., RED and infrared (IR) light, into the tissue of a patient 36, where the RED wavelength may be between about 600 nm and about 700 nm, and the IR wavelength may be between about 800 nm and about 1000 nm. The emitter 30 may include a single emitting device, for example, with two light emitting diodes (LEDs) or the emitter 30 may include a plurality of emitting devices with, for example, multiple LED's at various locations. Regardless of the number of light emitting devices, the emitter 30 may be used to measure, for example, blood oxygen saturation, water fractions, hematocrit, and/or other physiologic parameters of the patient 36, as discussed herein. It should be understood that, as used herein, the term "light" may refer to one or more of radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use in accordance with the present disclosure.

In one embodiment, the detector 32 may be an array of detector elements that may be capable of detecting light at various intensities and wavelengths. In operation, light enters the detector 32 after passing through the tissue of the patient 36. The detector 32 may convert the light at a given intensity, which may be directly related to the absorbance and/or reflectance of light in the tissue of the patient 36, into an electrical signal. That is, when more light at a certain wavelength is absorbed or reflected, less light of that wavelength is typically received from the tissue by the detector 32. For example, the detector 32 may include one or more photodiodes, or any other element capable of converting light into either a current or voltage. After converting the received light to an electrical signal, the detector 32 may send the signal, which may be a plethysomographic ("pleth") signal, to the monitor 10, where physiological characteristics may be calculated based at least in part on the absorption of light in the tissue of the patient 36.

In some embodiments, the sensor 28 may include an encoder 34, which may contain information about the sensor 24, such as what type of sensor it is (e.g., whether the sensor is intended for placement on a forehead or digit) and the wavelengths of light emitted by the emitter 30. Further, the encoder 34 may contain information about dividing specific physiological characteristics (e.g., respiration rate and/or blood pressure) into tiers for monitoring and alarm threshold and sensitivity levels associated with those tiers. This information may allow the monitor 10 to select appropriate algorithms and/or calibration coefficients for calculating the patient's physiological characteristics. The encoder 34 may, for instance, be a memory on which one or more of the following information may be stored for communication to the monitor 10: the type of the sensor 28; the wavelengths of light emitted by the emitter 30; the proper calibration coefficients and/or algorithms to be used for calculating the patient's physiological characteristics, and monitoring tiers for physiological characteristics (e.g., respiration rate and/or blood pressure) and/or alarm threshold and sensitivity levels associated with those tiers. In one embodiment, the data or signal from the encoder 34 may be decoded by a decoder 38 in the monitor 10.

Signals from the detector 32 and the encoder 34 may be transmitted to the monitor 10. The monitor 10 may include one or more processors 40 coupled to an internal bus 42. Also connected to the bus 42 may be a RAM memory 44 and a display 46. The monitor 10 may also include a modulator 48, which may include a time processing unit (TPU) 50 and light drive circuitry 52. The modulator 48 may modulate the drive signals that activate the LEDs or other emitting structures of the emitter 30. The modulator 48 may be hardware-based, software-based, or some combination thereof. For example, a software aspect of the modulator 48 may be stored on the memory 44 and may be controlled by the processor 42. The TPU 50 may include a sine wave generator, and may provide timing control signals to light drive circuitry 52, which controls when the emitter 30 is activated, and if multiple light sources are used, the multiplexed timing for the different light sources. TPU 50 may also control the gating-in of signals from detector 32 through a switching circuit 54. These signals are sampled at the proper time, depending at least in part upon which of multiple light sources is activated, if multiple light sources are used.

The received signal from the detector 32 may be processed to provide certain physiological data. In one embodiment, the received signal may be passed through an amplifier 56, a low pass filter 58, and an analog-to-digital converter (ADC) 60 for amplifying, filtering, and digitizing the electrical signals received from the sensor 24. The digital data may then be stored in a queued serial module (QSM) 62, for later downloading to RAM 44 as QSM 62 fills up. There may also be multiple parallel paths for separate amplifiers, filters, and A/D converters for multiple light wavelengths or spectra received. Further, the processor 40 may calculate the oxygen saturation based on the received signals corresponding to the light received by the detector 32. For example, the processor 40 may perform instructions or algorithms stored on the memory 64, and may be configured to perform calculations to estimate physiological parameters based on the received signals. For example, physiological parameters, such as respiration rate and blood pressure, may be calculated and monitored as described herein in embodiments depicted in FIGS. 3-11 and FIGS. 12-17, respectively.

Figure 3:
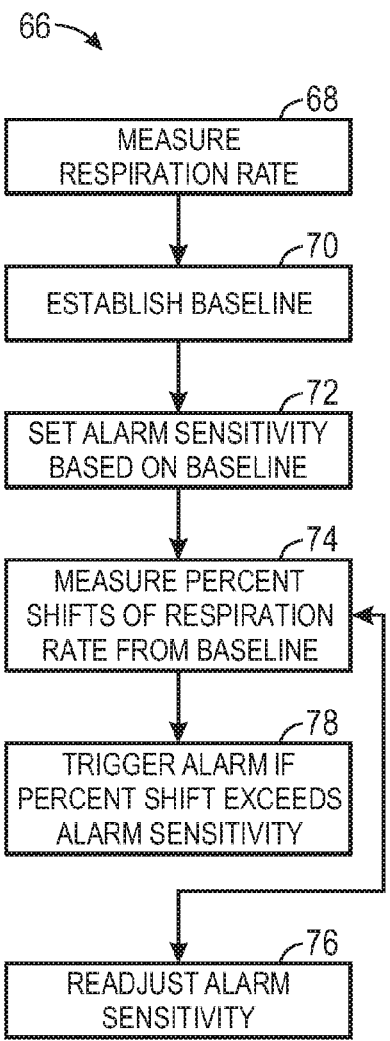
FIG. 3 is a flow chart depicting an embodiment of a method for monitoring respiration rate.

For instance, FIG. 3 depicts an embodiment of a method 66 for monitoring respiration rate. In general, the method 66 may begin by measuring respiration rate (block 68). Upon measuring the respiration rate, a respiration rate baseline may be established (block 70). The monitor 10 may automatically establish a respiration rate baseline within a set time window upon measuring the respiration rate (e.g., 30 seconds). However, the caregiver may want to establish the baseline at a particular time or event (e.g., before or after administering anesthesia). To do this the caregiver may manually input into the monitor 10 when to establish the baseline via the control inputs 26 provided on the monitor 10.

Based on the respiration rate baseline, the monitor 10 may set the alarm sensitivity (block 72). The alarm sensitivity may fall into multiple tiers. The tiers may include an upper tier, a middle tier, and a lower tier. The upper tier may be for patients 36 with specific conditions that may be associated with rapid breathing (e.g., pneumonia or a pulmonary embolism). The middle tier may be for relatively normal patients 36 who are not experiencing any breathing problems. The lower tier may be for patients 36 with specific conditions associated with slow breathing (e.g., a metabolic disorder or cancer). For example, the alarm sensitivity tiers may be divided as follows: 6 breaths per minute (bpm) and below for the lower tier, 7 bpm to 29 bpm for the middle tier, and 30 bpm and above for the upper tier. Respiratory rates may vary based on numerous factors such as age, health, and activity. The respiratory rate ranges above may reflect these factors. For example, as to the lower tier, 6 bpm and below may reflect an abnormally low respiratory rate which might concern a caregiver. As to the middle tier, 7 bpm to 29 bpm may reflect a wide range of normal respiratory rate activity. The normal respiration rate for each individual varies significantly in the population, thus a wide range may be appropriate. As to the upper tier, 30 bpm and above may reflect a concern by the caregiver with abnormally high and dangerous changes in the respiratory rate.

Each tier may have a set sensitivity level. For example, the lower tier may have a sensitivity level of 20%, thus shifts of as little as one bpm may exceed the threshold. The sensitivity level for the lower tier may reflect a concern that a shift of only one bpm, mainly in the downward direction, may put the patient 36 at risk since the patient's breathing is already so low. Thus, the caregiver may want to be aware of any change in the patient's breathing in this tier. The middle tier may have a sensitivity level of 30%. This sensitivity level may reflect that the normal range for respiration is fairly broad and shifts within this range are of not as much concern to the caregiver as changes in respiration rate outside the normal range. While the caregiver may be interested with shifts in both downward and upward directions, the caregiver may be more concerned with shifts in respiration rate that approach the other tiers or take the respiration rate outside the middle tier. As to the upper tier, a 20% sensitivity may apply. In this tier, the caregiver may be mainly concerned with shifts in the upward direction since shifts downward reflect that the patient 36 may be breathing more normal. The sensitivity level may be set low, relative to the sensitivity level of the middle tier, because a patient's health may be at risk with such a high respiration rate and the caregiver may want to be aware of any change immediately.

After establishing the respiration rate baseline and setting the alarm sensitivity, the monitor 10 may measure percent shifts in the respiration rate from the baseline (block 74). The monitor 10 may measure percent shifts in the respiration rate to keep track of changes in the respiration rate of the patient 36 and to determine if the patient's respiration rate is deviating from the baseline respiration rate. As mentioned above, the percent shifts from the baseline respiration rate in the middle tier may be of less concern to the caregiver as percent shifts in the lower or upper tiers.

Based on the observed respiration rate, observed shifts in respiration rate from the baseline, and factors specific to the patient 36, a caregiver may manually readjust the alarm sensitivity to a desired sensitivity level (block 76). For example, the patient 36 may have been administered a drug that alters the respiration rate or the patient 36 may be undergoing some physical activity. In one embodiment, the caregiver may use the control inputs 26 to select a desired sensitivity level provided on the display screen 16 of the monitor 10. In a further embodiment, the monitor 10 may include a touch screen with a slide rule displaying a range of sensitivity levels with a graphical user interface to allow the user to easily adjust the sensitivity threshold by touching and moving an indicator up or down the slide rule to select the desired sensitivity threshold. Alternatively, the monitor 10 may automatically readjust the alarm sensitivity based upon a shift in the respiration rate from one tier into another tier. For example, if a patient's respiration rate begins in the lower tier and eventually the respiration rate falls within the middle tier, the sensitivity may be automatically readjusted from 20% to 30%, the sensitivity levels of the lower and middle tiers, respectively.

While monitoring the percent shifts in the respiration rate, the monitor 10 may trigger an alarm (block 78) if the percent shift in the respiration rate exceeds the alarm sensitivity for that tier. The alarm may be a vocal, visual, or text alarm depending on the tier. For example, in the lower tier if the respiration rate shifts 20% (e.g., 5 bpm to 4 bpm) maybe both a visual alarm and a vocal alarm may be given to get the immediate attention of the caregiver that the patient 36 may be experiencing a serious problem. Similarly, a shift in the upper tier of 20% (e.g., 30 bpm to 36 bpm) may also trigger both a visual alarm and a vocal alarm to get the immediate attention of the caregiver as to a problem with the patient 36. The monitor 10 may give the visual alarm on the display screen 16 or, alternatively, via one of the indicators 18. The visual alarm may be associated with a color such as red in either the upper tier or lower tier. The monitor 10 may give the vocal alarm via the speaker 20. Shifts in respiration rate in the middle tier may only give a visual or textual alarm since the caregivers may want to note the shift, but the presence of the caregiver may not be critical since the patient 36 is still relatively normal. The visual alarm for the middle tier may be associated with a color such as yellow. However, if shifts in the middle tier bring the respiration rate closer to the upper or lower tier, then maybe the visual alarm may be associated with a color such as orange to get the attention of the caregiver that the patient's respiration rate may be approaching potentially dangerous levels. If the shift in respiration rate exceeds the alarm sensitivity of the middle tier, while bringing the respiration rate into the upper or lower tier, the monitor 10 may trigger both a visual alarm (maybe associated with a red color) and a vocal alarm.

Figure 4:
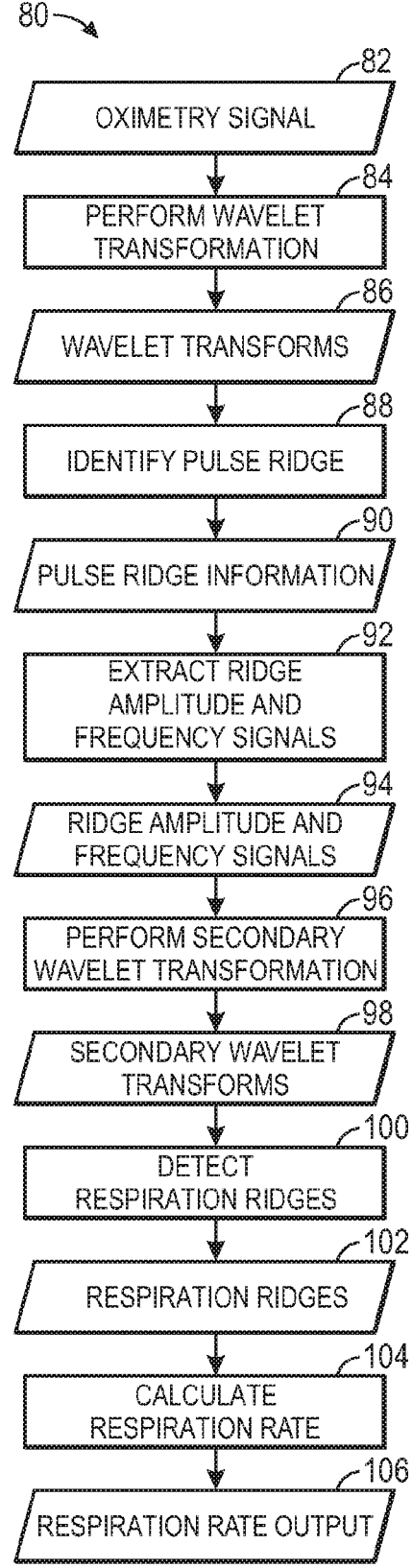
FIG. 4 is a flow chart depicting an embodiment of a method for measuring respiration rate.

It should be noted that, in order to measure respiration rate, embodiments of the present disclosure may utilize systems and methods such as those disclosed in U.S. application Ser. No. 10/547,430, filed Feb. 27, 2004, and U.S. application Ser. No. 10/480,983, filed Jun. 21, 2002, and each are incorporated herein by reference in their entirety for all purposes. FIG. 4 depicts an embodiment of a method 80 for measuring respiration rate. The monitor 10 may receive a pulse oximetry signal 82 (e.g., a pleth signal) from the sensor 24. Upon receiving the pulse oximetry signal 82, wavelet transformation may be performed (block 84) to generate wavelet tranforms 86. Then, pulse ridge information 90 may be identified (block 88) from various components of the wavelet transforms 86. The pulse ridge information 90 along with components of the wavelet transforms 86 may be used to extract (block 92) the amplitude and frequency signals 94 of the pulse ridge. Upon extracting the pulse ridge amplitude and frequency signals 94, a secondary wavelet transformation may be performed (block 96) to generate secondary wavelet transforms 98. Detecting respiration ridges (block 100) from the secondary wavelet transforms 98 may then occur. From the respiration ridges 102 a respiration rate may then be calculated (block 104) to generate a respiration rate output 106.

Figure 5:
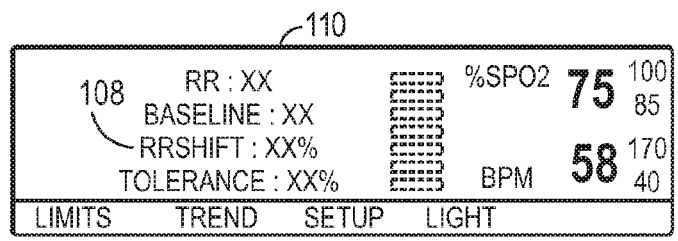
FIG. 5 is a representation of an embodiment of a screen displaying a graphical indicator related to respiration rate.

Once the respiration rate is determined, the caregiver may be notified via a graphical indicator 108 of data related to respiration rate. FIG. 5 illustrates an embodiment of a display 110, where the graphical indicator 108 may be represented in a textual form. The graphical indicator 108 may include respiration rate, baseline respiration rate, percent shift in the respiration rate from the baseline respiration rate, and/or the current tolerance or sensitivity level as a percentage. The tolerance or sensitivity level may set the threshold for triggering respiration rate-associated alarms.

Figure 6:
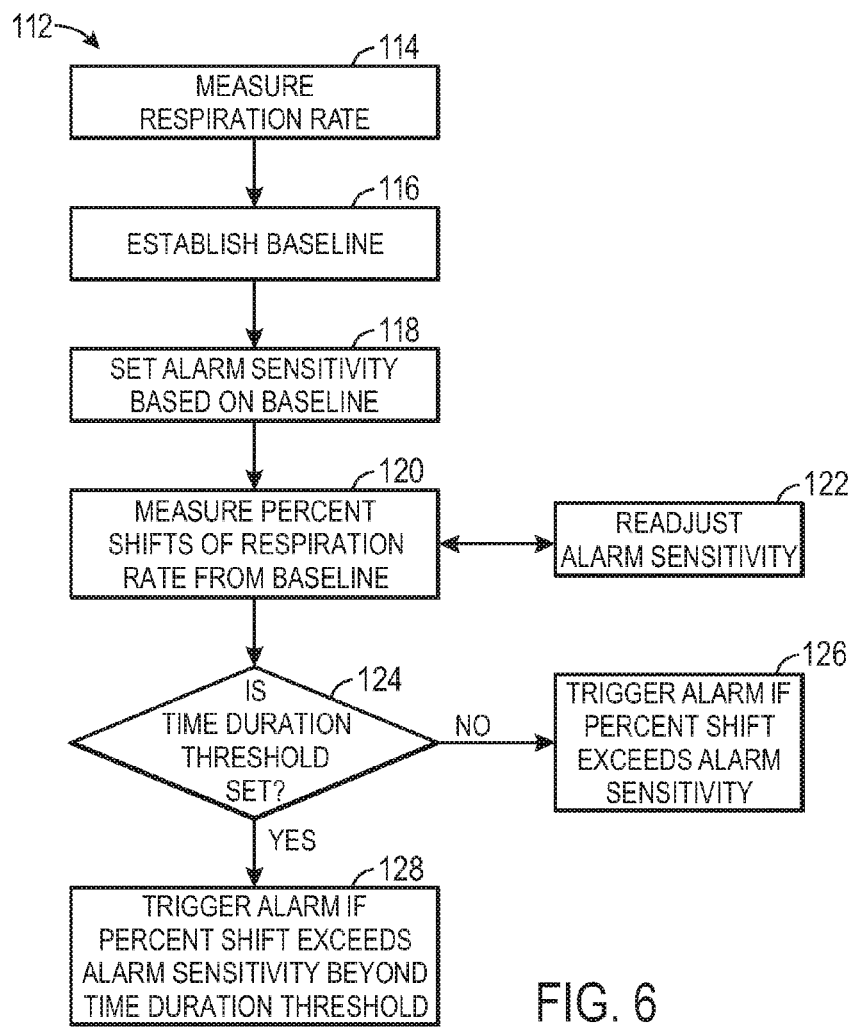
FIG. 6 is a flow chart depicting an embodiment of a method for managing a respiration rate alarm.

FIG. 6 depicts another embodiment of a method 112 for monitoring respiration rate. Similar to the method 66 described above, the method 112 may begin by measuring respiration rate (block 114). Upon measuring the respiration rate, a respiration rate baseline may be established (block 116) manually or automatically as described above. Based on the respiration rate baseline, the monitor 10 may set the alarm sensitivity (block 118). The alarm sensitivity may fall into multiple tiers with each tier having a set sensitivity level as described above. After establishing the respiration rate baseline and setting the alarm sensitivity, the monitor 10 may measure percent shifts in the respiration rate from the baseline (block 120). As described above, the alarm sensitivity may be readjusted (block 122) manually or automatically.

However, unlike the method 66, the method 112 may include a time duration threshold. The time duration threshold may analyze the duration (seconds) of a percent shift in respiration rate from the baseline respiration rate that exceeds the sensitivity level. If the time duration of the percent shift exceeds the sensitivity level for a set time this may trigger a respiration rate-associated alarm. Accordingly, sudden short shifts exceeding the sensitivity level that would normally trigger nuisance alarms may be eliminated while more prolonged shifts exceeding the sensitivity level may be counted. Caregivers may set the time duration threshold for 15, 30, 45, or 60 seconds, for example. Alternatively, the monitor 10 may automatically set the time duration threshold for a time specific to the sensitivity level or tier. Thus, upon measuring percent shifts in the respiration rate from the respiration rate baseline (block 120), the monitor 10 may establish if the time duration threshold is set (block 124). If the time duration threshold is not set, an alarm may be triggered (block 126) if the percent shift in the respiration rate exceeds the alarm sensitivity. If the time duration threshold is set, an alarm may be triggered (block 128) if the percent shift in the respiration rate exceeds the alarm sensitivity beyond the set time duration threshold. As mentioned above, the alarm may be a vocal, visual, or text alarm. Also, as above, the specific type of alarm and any color associated with the alarm may depend on the tier.

Figure 7:
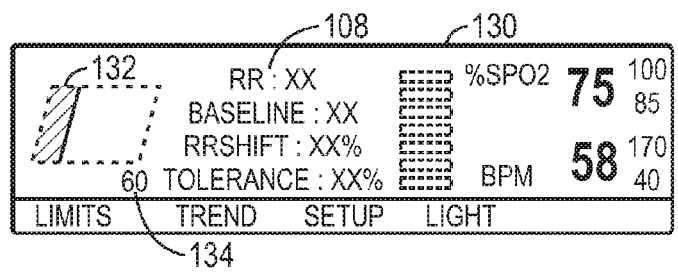
FIG. 7 is a representation of an embodiment of a screen displaying a graphical indicator related to respiration rate.

Besides data related to respiration rate, the caregiver also may be notified via a graphical indicator 132 of the time duration threshold. FIG. 7 illustrates an embodiment of a display 130 similar to FIG. 5. The display 130 may include the graphical indicator 108 representing data related to respiration rate in textual form as described above. In addition, the display 130 may include the graphical indicator 132 for the time duration threshold. The graphical indicator 132 may be represented on the display 130 as a dashed parallelogram that may graphically fill from left to right as the monitored time duration for a percent shift in respiration rate from the respiration baseline exceeding the sensitivity level increases. For example, the graphical indicator 132 may be full when the count reaches 60 seconds upon which a respiration rate-associated alarm may be triggered. Alternatively, the graphical indicator 132 may be represented by another dashed shape such as a triangle, circle, square, or any other shape. Further, the graphical indicator may include an indicator 134 of the set time for the time duration threshold.

In addition to a module for managing a respiration rate alarm, some embodiments of a patient monitor 10 may employ other alarm management modules such as SatSeconds™ and OxiMax SPD™ by Nellcor™. SatSeconds™ may include activation of an alarm based on limits that may include the integral of time and depth of a desaturation event and may include an indicator that may serve to inform the caregiver that an $SpO_2$ reading has been detected outside of the limit settings. According to certain embodiments, the SatSeconds™ alarm management feature may analyze $SpO_2$ excursions outside of the alarm limits to differentiate between clinically significant desaturations and minor transient events. For example, SatSeconds™ may enable oxygen saturation alarms only when a SatSeconds™ value, represented by a combination of the magnitude and time of the oxygen saturation excursion, exceeds a certain threshold. In general, the SatSeconds™ value may be the product of the magnitude and duration of an oxygen desaturation event. Accordingly, shallow and/or short desaturation readings that may be measurement noise (e.g., that otherwise may trigger nuisance alarms) may not produce an alarm, allowing caregivers to put brief desaturation events into context with their depth and to put shallow desaturations into context with their duration. In summary, the SatSeconds™ alarm management feature may filter out nuisance alarms to produce a higher ratio of alarms when a clinically significant excursion occurs, as determined by the SatSeconds™ setting. For example, the SatSeconds™ value may be set to 10, 25, 50 or 100 SatSeconds™, with 100 SatSeconds™ representing the highest threshold for producing an alarm and 10 SatSeconds™ representing the lowest threshold for producing alarms. For example, when the SatSeconds™ value is set to 100 only events that equal or surpass the 100 SatSeconds™ limit may trigger an oxygen saturation alarm.

As mentioned, the patient monitor 10 also may employ an OxiMax SPD™ alert by Nellcor™ to detect patterns of desaturation that are indicative of repetitive reductions in airflow. For example, the OxiMax SPD™ alarm management feature may analyze oxygen saturation trend data to determine if apnea is present. A Saturation Pattern Detection ("SPD") indicator may provide information to a user related to the occurrence, frequency, and/or magnitude of the patterns detected. As patterns are detected, an index value may increase until the alarm threshold is reached, resulting in an alarm. For example, the index value may be a scoring index, such as a Saturation Pattern Detection index (SPDi), which may represent the magnitude and variability of ventilator variations detected by patterns in the oxygen saturation values. In certain embodiments, the SPDi may be calculated using features such as the magnitude of the $SpO_2$ pattern, the variability in the $SpO_2$ peaks, and the variability in the nadir. In these embodiments, the graphical indicator may gradually fill as the SPDi index increases.

The OxiMax SPD™ alert may include several tolerance settings that may be selected by a user. For example, the tolerance setting may be set to low (level 1), medium (level 2), or high (level 3). Under the high tolerance setting only the most severe apnea patterns may produce an SPD alarm while under the low tolerance setting, even the least severe patterns may trigger an SPD alarm. When the SPD™ indicator is full, the tolerance setting may have been reached or exceeded, and the patient monitor 10 may produce an alarm.

Figure 8:
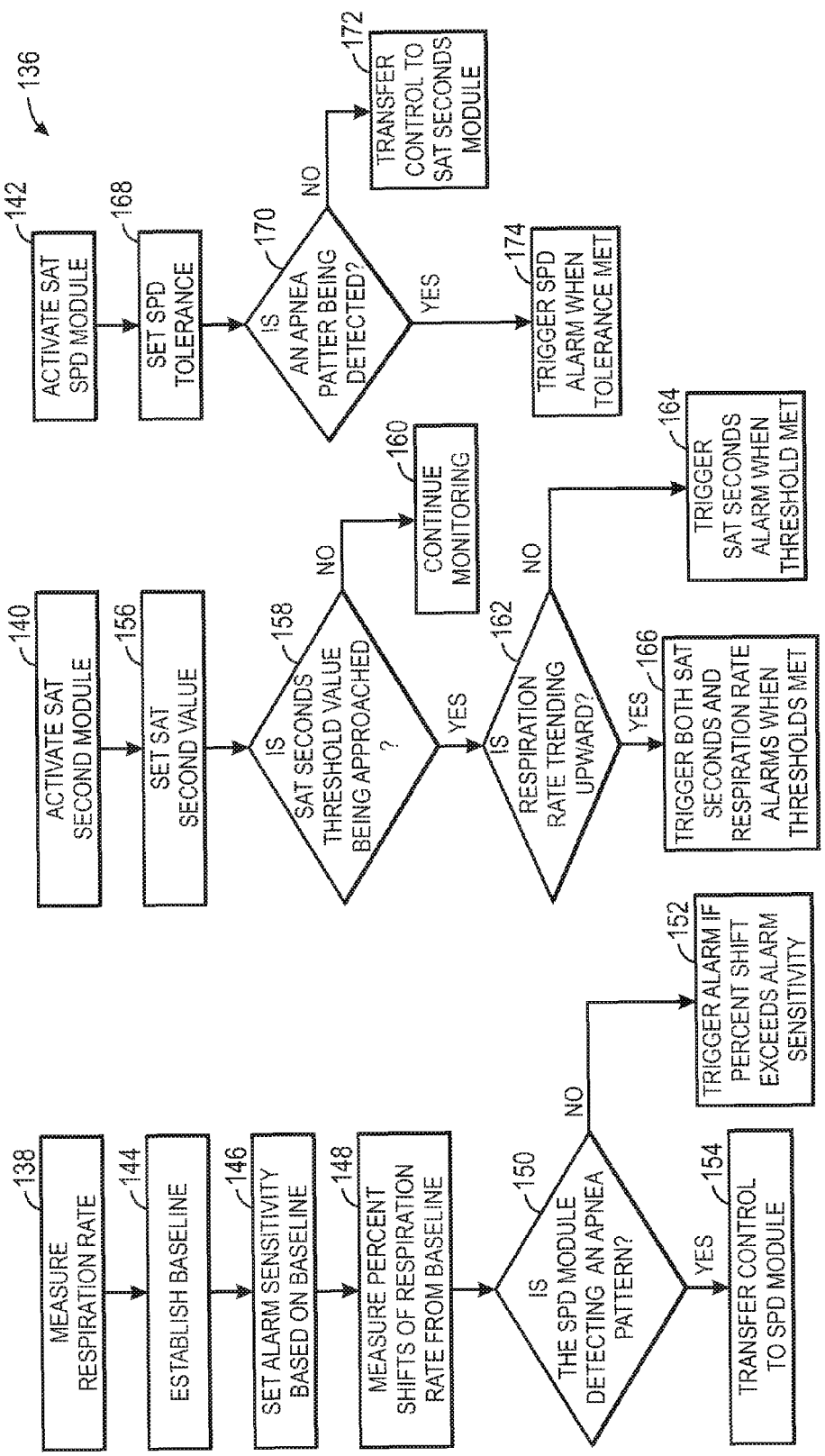
FIG. 8 is a flow chart depicting an embodiment of a method for managing multiple alarms.

In embodiments featuring multiple alarm modules, the alarm modules may be managed to provide the caregiver a clearer indicator of what condition the patient is actually experiencing. For example, an alarm module may be triggered (e.g., the SatSeconds™ module), when another alarm module (e.g., the SPD™ module) is more relevant to the condition experienced by the patient 36 (e.g., sleep apnea). FIG. 8 depicts an embodiment of a method 136 for managing multiple alarms. The method 136 may include measuring respiration rate (block 138), activating a SatSeconds™ module (block 140), and activating a SPD™ module (block 142). Upon measuring the respiration rate (block 138), a respiration rate baseline may be established (block 144) manually or automatically as described above. Based on the respiration rate baseline, the monitor 10 may set the alarm sensitivity (block 146). The alarm sensitivity may fall into multiple tiers with each tier having a set sensitivity level as described above. After establishing the respiration rate baseline and setting the alarm sensitivity, the monitor 10 may measure percent shifts in the respiration rate from the baseline (block 148).

Figure 10A:
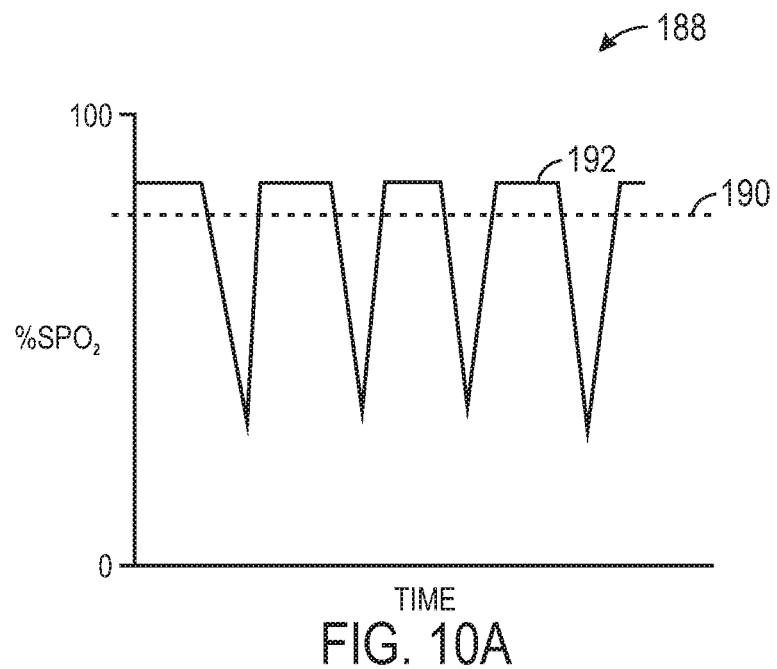
FIG. 10(a) is a representation of a graph including an $SpO_2$ trend that contains an apnea $SpO_2$ pattern.
Figure 10B:
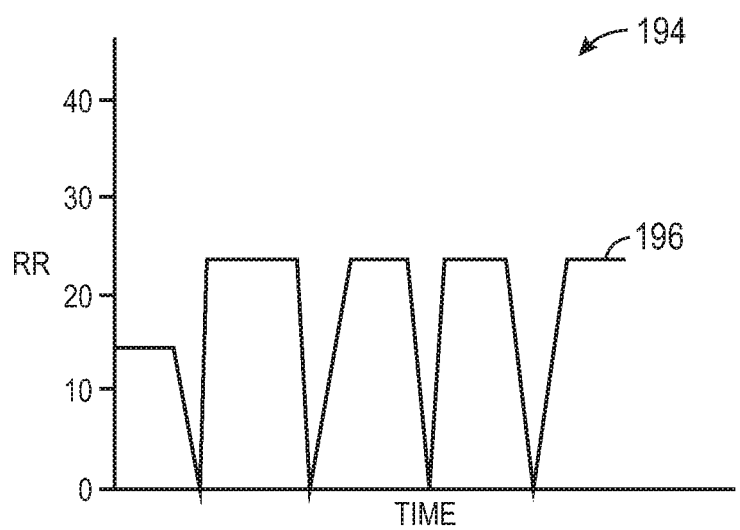
FIG. 10(b) is a representation of a graph including a respiration rate trend corresponding to the $SpO_2$ pattern in FIG. 10(a)

Upon measuring the respiration rate, the monitor 10 may then determine if the SPD™ module is detecting an apnea pattern (block 150). Determining if an apnea pattern is being detected may help determine whether to continue control with the respiration rate-associated module or to shift control to the SPD™ module. For example, FIG. 10(a) depicts a representation of a graph 188 including an $SpO_2$ trend that includes an $SpO_2$ pattern indicative of an apnea event. The repeated sharp departures below a limit 190 and return to above the limit 190 by a pleth 192 representative of oxygen saturation represents a typical apnea pattern that may be experienced by a patient 36. FIG. 10(b) illustrates a graph 194 of a corresponding trend in the respiration rate with sharp declines and increases as shown by line 196. These sharp declines and increases in respiration rate may trigger the alarm for the respiration rate-associated module. However, the condition experienced by the patient 36 may not be reflective of a patient 36 who might be suffering from a true respiratory condition, but a relatively normal patient 36 experiencing episodes of apnea. Thus, if the SPD™ module is not detecting an apnea pattern, then control may remain with the respiration rate-associated module and an alarm may be triggered (block 152) if the percent shift in the respiration rate exceeds the alarm sensitivity. However, if the SPD™ module is detecting an apnea pattern, then control is transferred (block 154) from the respiration rate module to the SPD™ module to give a better indication to the caregiver of what is happening with the patient 36.

Figure 11A:
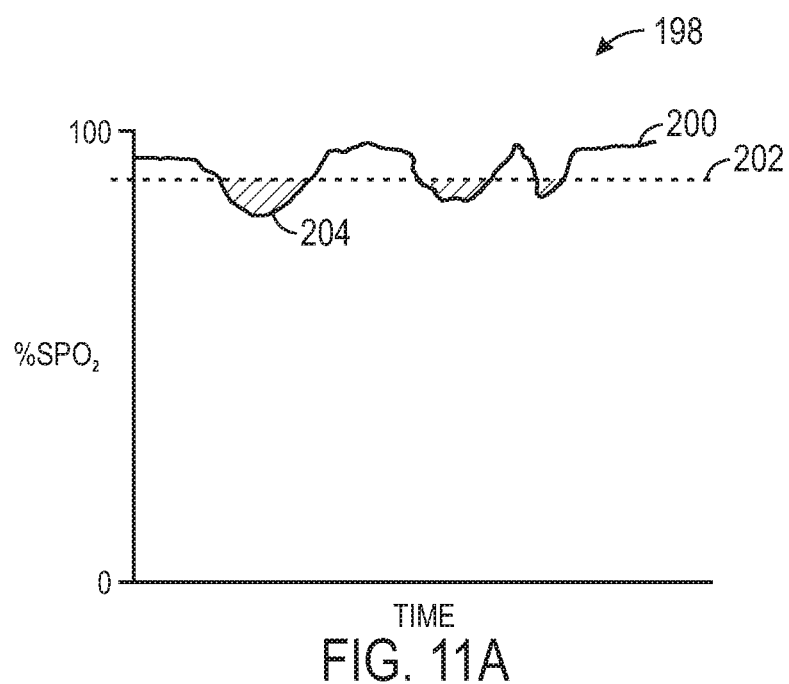
FIG. 11(a) is a representation of a graph including an $SpO_2$ trend that contains a normal $SpO_2$ pattern.
Figure 11B:
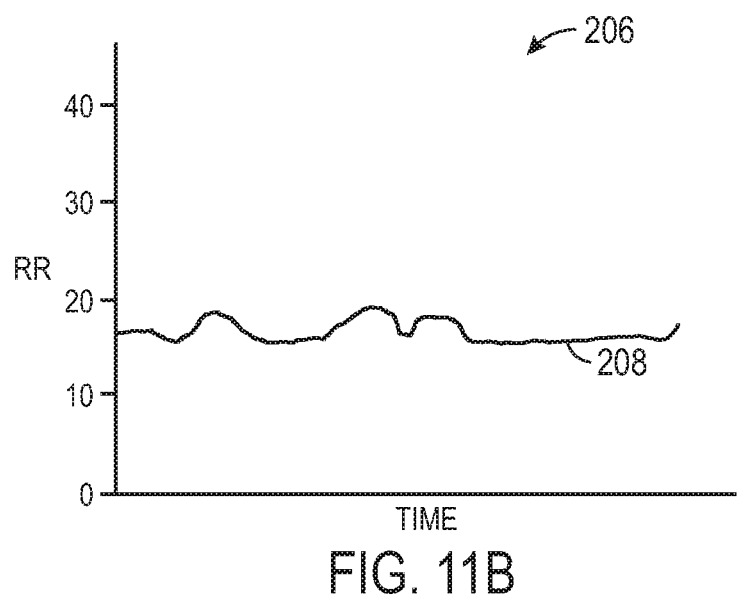
FIG. 11(b) is a representation of a graph including a respiration rate trend corresponding to the $SpO_2$ pattern in FIG. 11(a)

Besides monitoring respiration rate, activation of the SatSeconds™ module (block 140) may occur and a SatSeconds™ value may be set (block 156). As mentioned above, the SatSeconds™ module may help determine if a patient 36 is experiencing a clinically significant desaturation event. Next, the monitor 10 may then decide if the SatSeconds™ threshold value is being approached (block 158). If the SatSeconds™ threshold value is not being approached, then monitoring may continue (block 160). For example, FIG. 11(a) depicts a representation of a graph 198 including one $SpO_2$ trend in which the pleth 200 may occasionally dip below the limit 202 as indicated by the shaded areas 204; however, these minor transient events may not amount to clinically significant desaturation events. If the SatSeconds™ threshold value is being approached, then the monitor 10 may then determine if the respiration rate is trending upward (block 162). An upward trend in respiration rate may be an indicator that the patient 36 may be suffering from some event in need of medical attention. Normally, in healthy patients 36 the respiration rate and the $SpO_2$ levels may correspond. For example, FIG. 11(b) illustrates a graph 206 of a corresponding trend in the respiration rate with minor deviations in the respiration rate as represented by line 208. As FIG. 11(b) illustrates, the respiration rate corresponds to some degree with the $SpO_2$ trend in FIG. 11(a). Thus, if the respiration rate is not trending upward, then the SatSeconds™ module may trigger an alarm only if the threshold value is met (block 164).

Figure 9A:
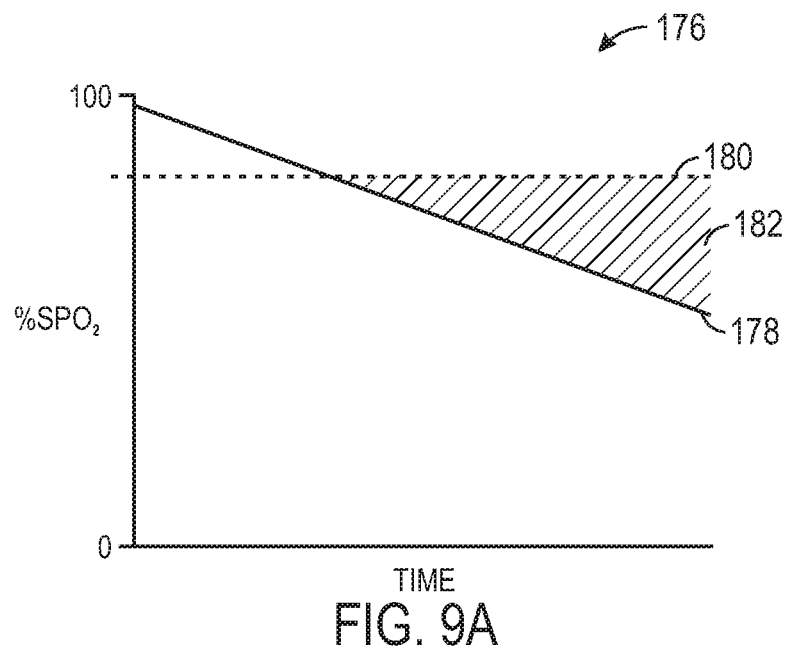
FIG. 9(a) is a representation of a graph including an $SpO_2$ trend that contains a declining $SpO_2$ pattern.
Figure 9B:
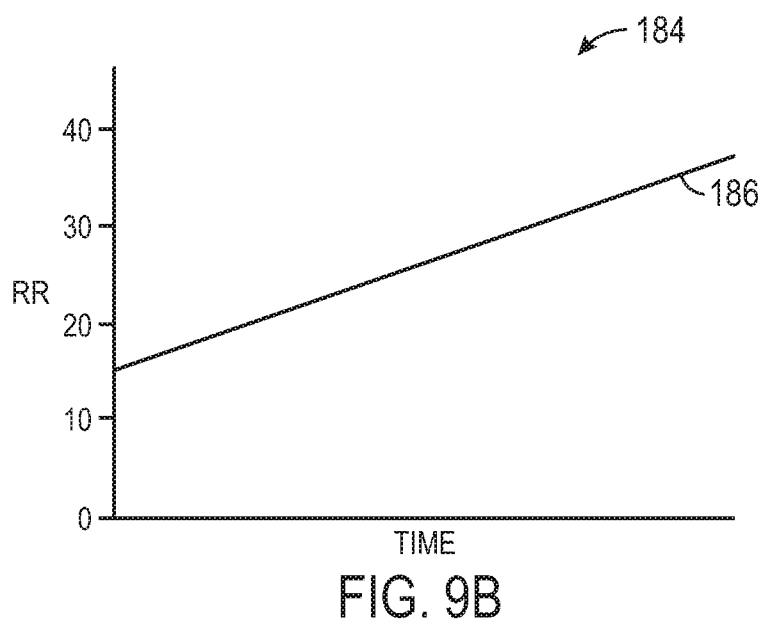
FIG. 9(b) is a representation of a graph including a respiration rate trend inverse to the $SpO_2$ pattern in FIG. 9(a)

However, if the respiration rate is trending upward, then the SatSeconds™ module may trigger an alarm if the threshold value is met and the respiration rate module may trigger an alarm if the percent shift in respiration rate from the respiration rate baseline exceeds the alarm sensitivity (block 166). This may occur, for example, in patients 36 experiencing a pulmonary embolism. For example, FIG. 9(a) depicts a representation of a graph 176 including an $SpO_2$ trend that contains a declining $SpO_2$ pattern. The graph 176 includes a pleth waveform 178 representative of oxygen saturation. As the pleth 178 falls below the set oxygen saturation limit 180, the SatSeconds™ module begins monitoring the event as indicated by the shaded area 182 below the limit 180. As mentioned above, normally the $SpO_2$ levels and respiration rate correspond in healthy patients. However, FIG. 9(b) illustrates a graph 184 of an inverse trend in the respiration rate showing an increase in the respiration rate as represented by line 186.

Thus, the patient 36 suffering from the pulmonary embolism may show a decrease in $SpO_2$ levels and an increase in respiration rate. In such an event, both the SatSeconds™ alarm and the respiration rate-associated alarm may be triggered when the respective thresholds for the alarms have been met.

In addition to monitoring respiration rate and activating the SatSeconds™ module, the SPD™ module (block 142) may be activated and a SPD™ tolerance may be set (block 168). The monitor 10 may then decide if an apnea pattern is being detected (block 170), such as illustrated in FIG. 10(a). Determining if an apnea pattern is being detected may help determine whether to maintain control with the SPD™ module or to shift control to the SatSeconds™ module. These sharp declines and increases in $SpO_2$ levels may trigger the alarm for the SatSeconds™ module. However, the condition experienced by the patient 36 may not be reflective of a patient 36 who might be suffering from a condition in need of immediate attention, but a relatively normal patient 36 experiencing episodes of apnea. Thus, if an apnea pattern is not being detected, then control may be transferred (block 172) to the SatSeconds™ module. However, if an apnea pattern is being detected, then the SPD™ module may trigger an alarm if the tolerance level is met (block 174).

Figure 12:
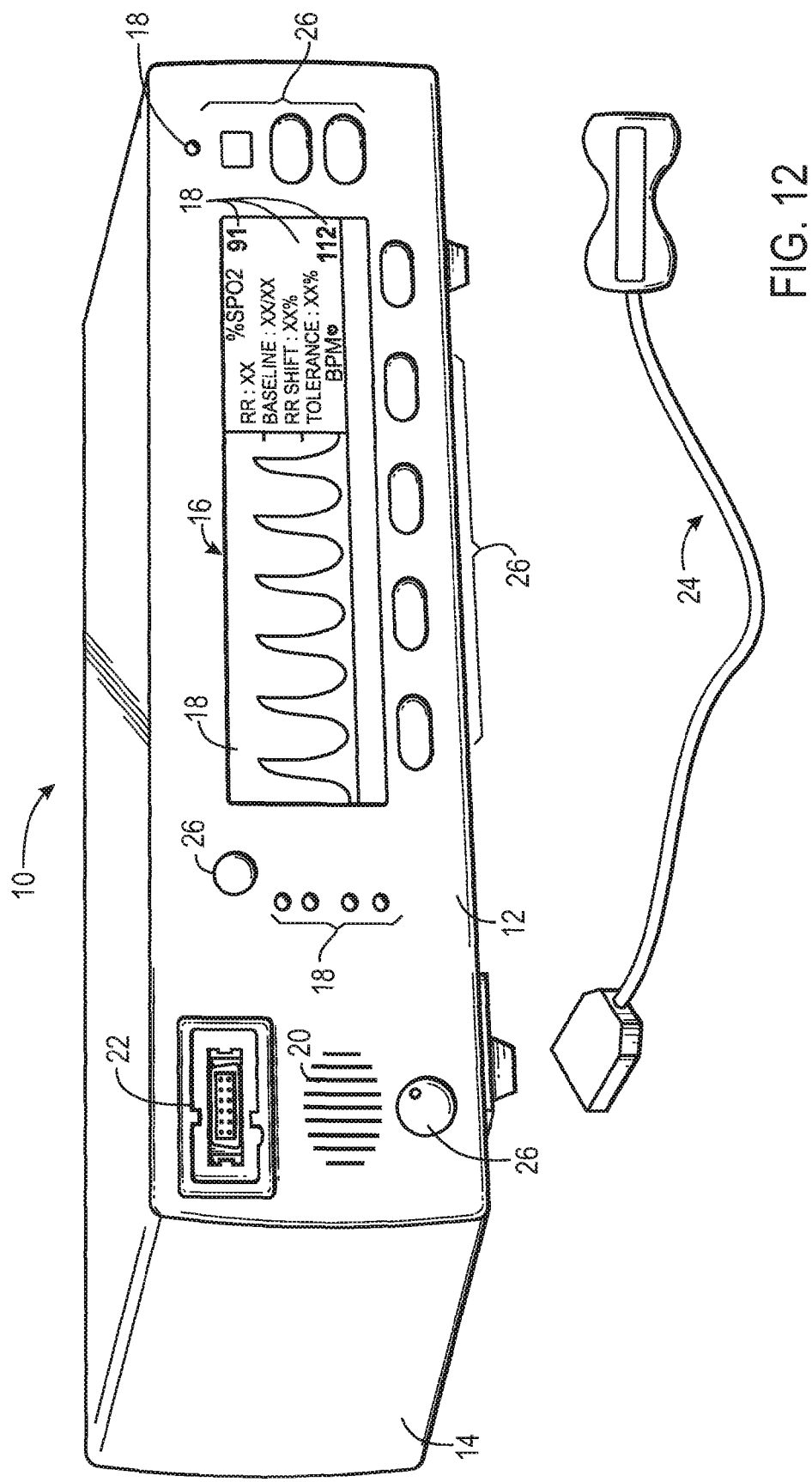
FIG. 12 is a perspective view of an embodiment of a patient monitor.

Besides monitoring respiration rate, as mentioned in the above embodiments, other physiological parameters may be monitored, such as blood pressure. FIG. 12 is a perspective view of a patient monitor 10 in accordance with another embodiment of the present disclosure. The patient monitor 10 may be similar to embodiments described above. As mentioned above, some of the indicators 18 on the monitor 10 are specifically provided to facilitate monitoring of a patient's physiological parameters. In embodiments, the indicators 18 may include an indicator related to blood pressure. In an embodiment, the indicator 18 may be a blood pressure indicator that provides an indication related to shifts in blood pressure.

Figure 13:
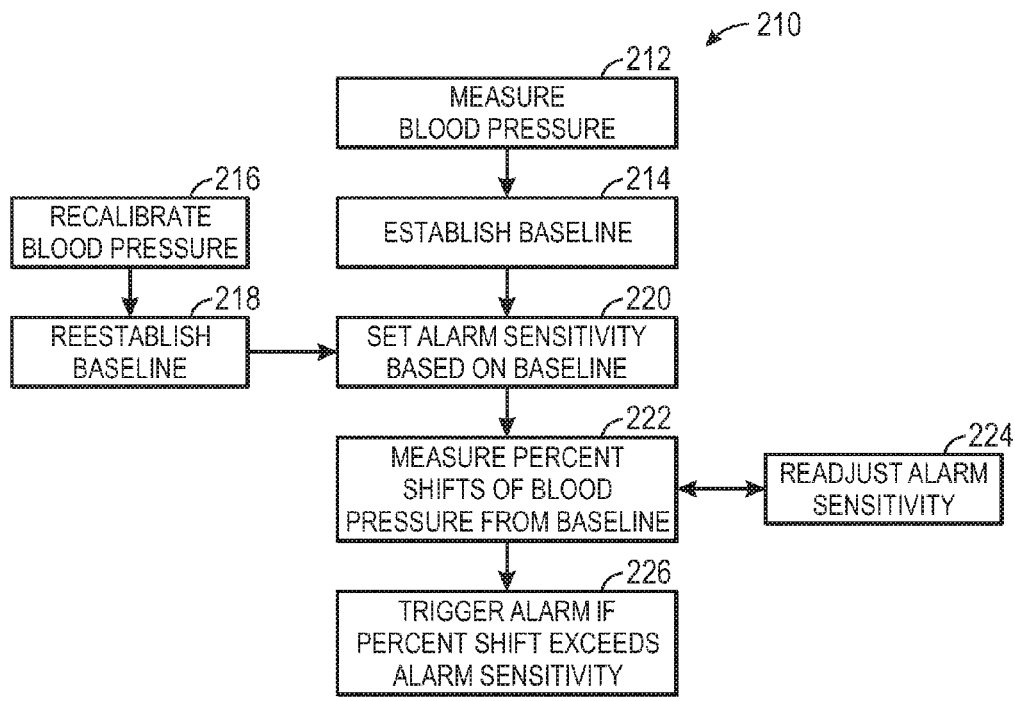
FIG. 13 is a flow chart depicting an embodiment of a method for monitoring blood pressure.

FIG. 13 depicts an embodiment of a method 210 for monitoring blood pressure. In general, the method 210 may begin by measuring blood pressure (block 212). Upon measuring the blood pressure, a blood pressure baseline may be established (block 214) for both systolic and diastolic blood pressures. The monitor 10 may automatically establish a blood pressure baseline within a set time window upon measuring the blood pressure (e.g., 30 seconds). However, the caregiver may want to establish the baseline at a particular time or event (e.g., before or administering a drug). To do this the caregiver may manually input into the monitor 10 when to establish the baseline via the control inputs 26 provided on the monitor 10.

Occasionally the blood pressure baseline may be recalibrated (block 216). Blood pressure may be determined by monitoring the pulse transit time. The condition of a patient 36 may vary over time (e.g., the administration of a vasoactive drug) affecting the relationship between blood pressure and pulse transit time. Thus, the monitor 10 may monitor multiple parameters to determine if the measurement of the blood pressure needs to be recalibrated. Recalibration may involve obtaining a reference blood pressure measurement using alternative devices to obtain the patient's blood pressure (e.g., a cuff-based system). Upon recalibration, the blood pressure baseline may be reestablished (block 218).

Based on the blood pressure baseline, the monitor 10 may set the alarm sensitivity (block 220). Alarm sensitivities may be set for both the systolic and diastolic blood pressures. The alarm sensitivity may fall into multiple tiers. The tiers may include a first tier, a second tier, a third tier, and a fourth tier. The first tier may be for patients 36 with relatively normal blood pressure. The second tier may be for patients 36 with blood pressure readings reflective of a pre-hypertensive state. The third tier may be for patients 36 with stage 1 high blood pressure and the fourth tier for patients 36 with stage 2 high blood pressure. For example, in adults the alarm sensitivity tiers may be divided as follows for systolic blood pressure: 119 mmHg and below, 120 mmHg to 139 mmHg, 140 mmHg to 159 mmHg, and 160 mmHg and above. For diastolic blood pressure, the alarm sensitivity tiers may be as follows: 80 mmHg and below, 81 mmHg to 89 mmHg, 90 mmHg to 99 mmHg, and 100 mmHg and above. A caregiver may be particularly concerned with the third and fourth tiers because high blood pressure may lead to coronary heart disease, heart failure, stroke, kidney failure, and other health conditions.

Each of the above tiers may have a set sensitivity level. For example, as relates to systolic blood pressure, the 119 mmHg and below may have a sensitivity level of 20%. In this tier, caregivers may be mainly concerned with drastic shifts in the downward direction, thus the larger sensitivity level. A drastic shift in the downward direction may result in hypotension. A drastic downward shift may be an indication of heart failure or a heart attack, for example. Occasionally, but rarely, the caregiver may be concerned with a rapid increase in blood pressure (e.g., malignant hypertension). The 120 mmHg to 139 mmHg tier may have a sensitivity level of 15%. In this tier, caregivers may be concerned with shifts in an upward direction since shifts in the upward direction may indicate the onset of hypertension. The 140 mmHg to 159 mmHg tier may have a sensitivity level of 10%. In this tier, once again caregivers may be concerned with shifts in an upward direction indicative of the onset of a severer stage of hypertension. As to the 160 mmHg and above tier, a level of 5% sensitivity may apply. In this tier, caregivers also may be mainly concerned with shifts in the upward direction as this may be indicative of a medical condition needing immediate condition.

As relates to diastolic blood pressure, the tiers may have similar sensitivity levels for the reason mentioned above for diastolic blood pressure. For example, the 80 mmHg and below tier may have a sensitivity level of 20%. In this tier, for the reasons mentioned above, the caregiver may be mainly concerned with drastic shifts in the downward direction. The 81 mmHg to 89 mmHg tier may have a sensitivity level of 15%. In this tier, caregivers may be concerned with shifts in an upward direction. The 90 mmHg to 99 mmHg tier may have a sensitivity level of 10%. In this tier, caregivers may be concerned with shifts in an upward direction. As to the 100 mmHg and above tier, a level of 5% sensitivity may apply. In this tier, caregivers may be mainly concerned with shifts in the upward direction.

The above tiers and the corresponding sensitivity levels may vary depending on time of day, age of patient, or health condition of patient. For example, the normal blood pressure for a neonate may differ from an adult. Also, if a patient 36 has a health condition a caregiver may want to use smaller sensitivity levels so that the caregiver may be aware of any change in the patient's condition. After establishing the blood pressure baseline and setting the alarm sensitivity, the monitor 10 may measure percent shifts in the blood pressure from the baseline (block 222). The monitor 10 may measure percent shifts in the blood pressure of the patient 36 and to see if the patient's blood pressure is deviating from the baseline blood pressure. As mentioned above, percent shifts from the baseline respiration rate may be of more concern in the third and fourth tiers with the exception of drastic downwards shifts in the first tier.

Based on the observed blood pressure, observed shifts in blood pressure from the baseline, and factors specific to the patient 36 (e.g., age, health condition, etc.), a caregiver may manually readjust the alarm sensitivity to a desired sensitivity level (block 224). For example, the patient 36 may have been administered a vasoactive drug that alters blood pressure or the patient 36 may be undergoing some physical activity. In one embodiment, the caregiver may use control inputs 26 to select a desired sensitivity level provided on the display screen 16 of the monitor 10. In a further embodiment, the monitor 10 may include a slide rule with a graphical user interface to allow the user to easily adjust the sensitivity threshold. In another embodiment, the monitor 10 may allow the user to enter the age of the patient, whereupon predetermined tiers and sensitivity levels may be selected. Also, the monitor 10 may automatically adjust the tiers and sensitivity levels based upon the time of day. Alternatively, the monitor 10 may automatically readjust the alarm sensitivity based upon a shift in the blood pressure from one tier into another tier. For example, if the systolic blood pressure begins in the first tier and eventually the systolic blood pressure falls within the second tier, the sensitivity may be automatically readjusted from 20% to 15%, the sensitivity levels of the first and second tiers.

While monitoring percent shifts in blood pressure, the monitor 10 may trigger an alarm (block 226) if the percent shift in either the systolic or the diastolic blood pressure exceeds the alarm sensitivity for that tier. The alarm may be a vocal, visual, or text alarm depending on the tier. For example, in the first tier if the systolic blood pressure shifts 20% (e.g., 119 mmHg to 95 mm Hg) just a visual alarm may be given. The monitor 10 may give the visual alarm on the display screen 16 or, alternatively, via one of the indicators 18. The visual alarm may be associated with a color such as yellow to alert the caregiver of the change. However, in the first tier if the shift in systolic blood pressure shifts 20% (e.g., 90 mmHg to 72 mmHg) both a visual alarm and vocal alarm may be given to get the immediate attention of the caregiver as to a problem with the patient 36 that may be causing the hypotension. The visual alarm may be associated with a color such as red to indicate the importance of the alarm. The monitor 10 may give the vocal alarm via the speaker 20. A shift in the second tier may raise an alarm for an upper shift in systolic blood pressure, for example. The alarm may be only a visual alarm. The color yellow may be associated with upward shifts, the color orange or red may be used for larger upward shifts into other tiers. The larger upward shifts may also generate a vocal alarm to get the caregiver's attention of a potentially dangerous change in the patient's health. As for the third and fourth tiers, shifts that trigger alarms may trigger both a visual and vocal alarm with the visual alarm associated with the color red.

Figure 14:
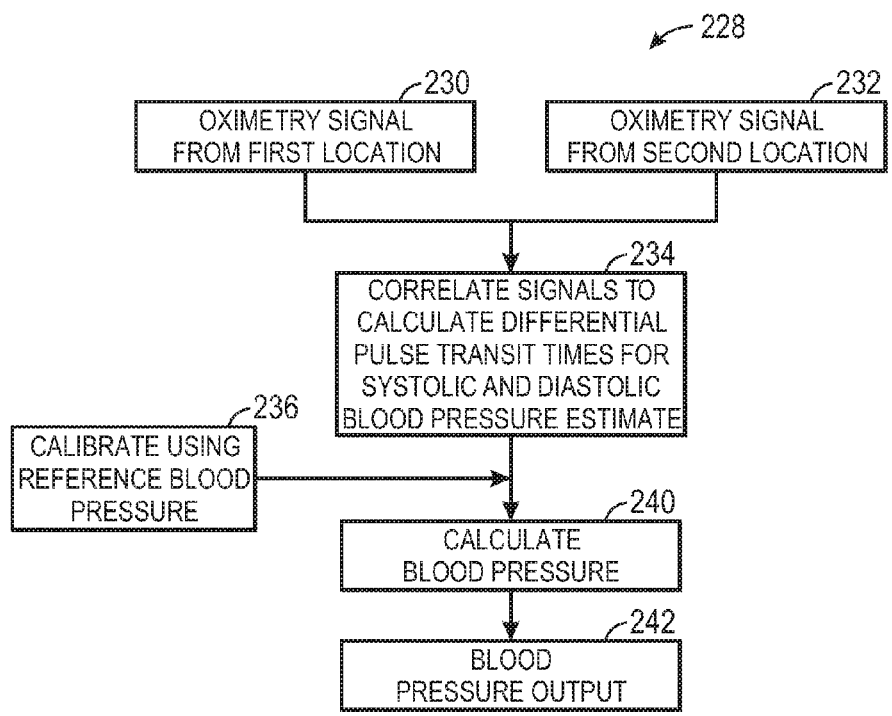
FIG. 14 is a flow chart depicting an embodiment of a method for measuring blood pressure.

It should be noted that, in order to measure blood pressure, embodiments of the present disclosure may utilize systems and methods such as those disclosed in U.S. Pat. No. 7,455,643 and U.S. Pat. No. 6,599,251, and each are incorporated herein by reference in their entirety for all purposes. FIG. 14 depicts an embodiment of a method 228 for measuring blood pressure. The monitor 10 may receive a pulse oximetry signal 230 (e.g., a pleth signal) from a first location of a sensor 24 and a pulse oximetry signal 232 from a second location of another sensor 24. Upon receiving the pulse oximetry signals 230 and 232, the monitor 10 may correlate the signals 230 and 232 (block 234) to calculate differential pulse transit times for systolic and diastolic blood pressure estimates. More specifically, the time difference between the peaks of signals 230 and 232 may allow an estimation of the systolic blood pressure. The time difference between the valleys of signals 230 and 232 may allow an estimation of the diastolic pressure. The monitor 10 may need to be calibrated using a reference blood pressure measurement (block 236) prior to using the data derived from the signals 230 and 232. The reference blood pressure measurement may already be stored on the monitor 10. Alternatively, the reference blood pressure measurement may be obtained from a separate device that measures blood pressure. The monitor 10 may calculate blood pressure (block 240) based upon the calibration information and the pulse transit times derived from the signals 230 and 232 to generate a blood pressure output 242.

Figure 15:
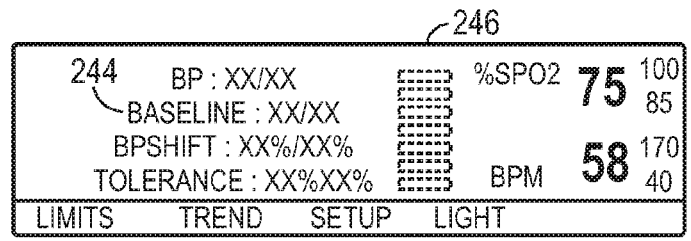
FIG. 15 is a representation of an embodiment of a screen displaying a graphical indicator related to blood pressure.

Once the blood pressure is determined, the caregiver may be notified via a graphical indicator 244 of data related to blood pressure. FIG. 15 illustrates an embodiment of a display 246, where the graphical indicator 244 may be represented in a textual form. The graphical indicator 244 may include systolic/diastolic blood pressures, baseline systolic/diastolic blood pressures, percent shifts in the systolic/diastolic blood pressures from the baseline blood pressures, and the current tolerance or sensitivity level as a percentage for both the systolic and diastolic blood pressures. The tolerance or sensitivity level may set the threshold for triggering blood pressure-associated alarms.

Figure 16:
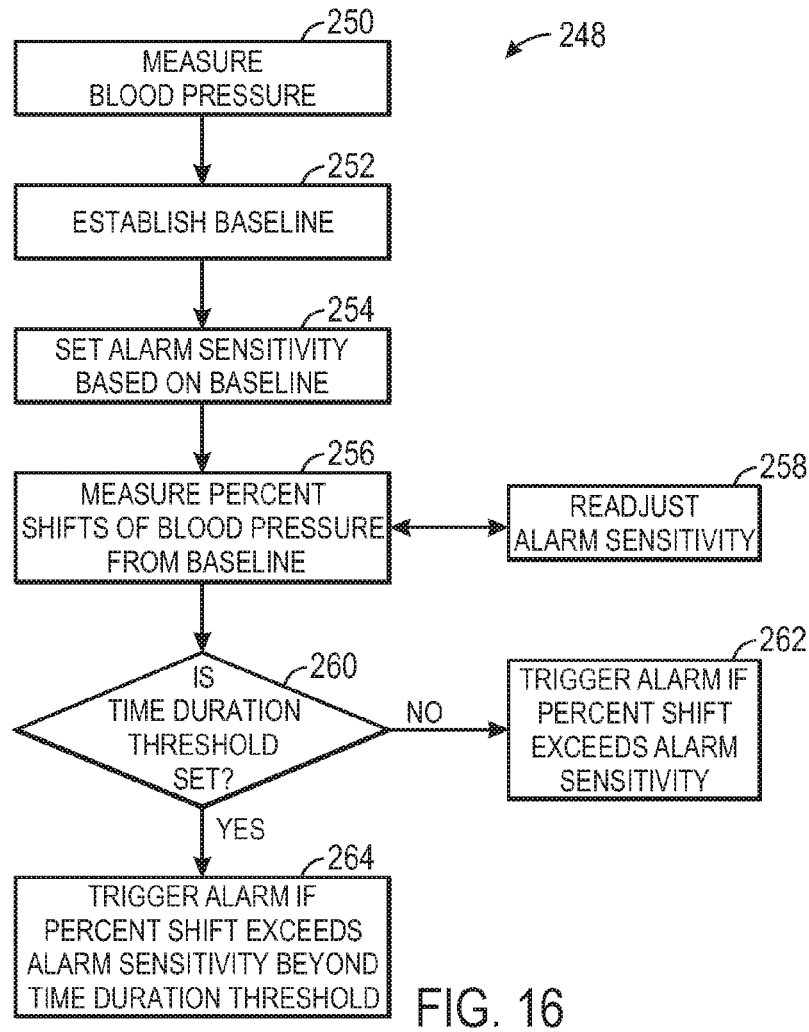
FIG. 16 is a flow chart depicting an embodiment of a method for managing a blood pressure alarm.

FIG. 16 depicts another embodiment of a method 248 for monitoring blood pressure. Similar to the method 210 described above, the method 248 may begin by measuring blood pressure (block 250). Upon measuring the blood pressure, a blood pressure baseline may be established (block 252) manually or automatically, as described above, for both systolic and diastolic blood pressures. Based on the blood pressure baselines, the monitor 10 may set the alarm sensitivity (block 254) for both systolic and diastolic blood pressures. The alarm sensitivity may fall into multiple tiers with each tier having a set sensitivity level as described above. After establishing the blood pressure baseline and setting the alarm sensitivity, the monitor 10 may measure percent shifts in the blood pressure from the baseline (block 256). As described above, the alarm sensitivity may be readjusted (block 258) manually or automatically.

However, unlike method 210, the method 248 may include a time duration threshold. The time duration threshold may analyze the duration (seconds) of a percent shift in blood pressure from the baseline blood pressure that exceeds the sensitivity level. If the time duration of the percent shift exceeds the sensitivity level for a set time this may trigger a blood pressure-associated alarm. Accordingly, sudden, short shifts exceeding the sensitivity level that would normally trigger nuisance alarms may be eliminated while more prolonged shifts exceeding the sensitivity level may be counted. Users may set the time duration threshold for 15, 30, 45, or 60 seconds. Alternatively, the monitor 10 may automatically set the time duration threshold for a time specific to the sensitivity level or tier. Thus, upon measuring percent shifts in the blood pressure from the blood pressure baseline (block 256), the monitor 10 may establish if the time duration threshold is set (block 260). If the time duration threshold is not set, an alarm may be triggered (block 262) if the percent shift in blood pressure exceeds the alarm sensitivity. If the time duration threshold is set, an alarm may be triggered (block 264) if the percent shift in blood pressure exceeds the alarm sensitivity beyond the set time duration threshold. As mentioned above, the alarm may be a vocal, visual, or text alarm. Also, as above, the specific type of alarm and any color associated with the alarm may depend on the tier.

Figure 17:
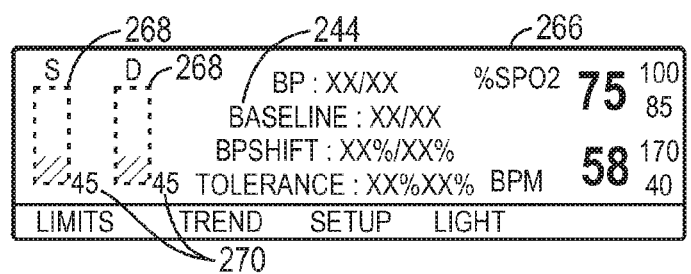
FIG. 17 is a representation of an embodiment of a screen displaying a graphical indicator related to blood pressure.

Besides data related to blood pressure, the caregiver also may be notified via a graphical indicator 268 for the time duration threshold. FIG. 17 illustrates an embodiment of a display 266 similar to FIG. 15. The display may include the graphical indicator 244 representing data related to blood pressure in textual form as described above. In addition, the display 266 may include a graphical indicator 268 for the time duration threshold for both the systolic and diastolic blood pressures. The graphical indicator 268 for both systolic and diastolic blood pressures may be represented on the display 266 as dashed vertically-oriented rectangles that may graphically fill from bottom to top as the monitored time duration for a percent shift in blood pressure from the blood pressure baseline exceeding the sensitivity level increases. The graphical indicator 268 may distinguish between the time duration thresholds for systolic and diastolic blood pressures with an S and a D above the respective rectangles for each blood pressure. For example, the graphical indicator 268 may be full when the count reaches 45 upon which a blood pressure-associated alarm may be triggered. Alternatively, the graphical indicator 268 may be represented by another dashed shape such as a triangle, circle, square, or any other shape. Further, the graphical indicator may include an indicator 270 of the set time for the time duration threshold.

While only certain features have been illustrated and described herein, many modifications and changes will occur to those skilled in the art. It is, therefore, to be understood that the appended claims are intended to cover all such modifications and changes as fall within their true spirit.

What is claimed is:

1. A method, comprising:
receiving an input from a sensor relating to one or more physiological parameters;
determining a blood pressure baseline from the input; and
establishing an alarm sensitivity for blood pressure based on the blood pressure baseline, wherein the alarm sensitivity comprises a first tier corresponding to a normal blood pressure range, a second tier corresponding to a pre-hypertensive blood pressure range, a third tier corresponding to a stage 1 high blood pressure range, and a fourth tier corresponding to a stage 2 high blood pressure range, wherein the alarm sensitivity relates to an acceptable percent shift of the blood pressure from the blood pressure baseline that if exceeded triggers an alarm, and the acceptable percent shift for at least one of the tiers is different from the acceptable percent shift of another one of the tiers.

2. The method of claim 1, comprising:
determining a blood pressure from the input; and
measuring a percent shift of the blood pressure from the blood pressure baseline.

3. The method of claim 2, wherein the input is a pulse oximetry signal and determining the blood pressure comprises deriving a differential pulse transit time from the pulse oximetry signal.

4. The method of claim 2, comprising triggering the alarm if the percent shift exceeds the established alarm sensitivity.

5. The method of claim 2, comprising triggering the alarm if the percent shift exceeds the established alarm sensitivity for a predetermined amount of time.

6. The method of claim 1, wherein the alarm sensitivity is selected based on which blood pressure range encompasses the blood pressure baseline.

7. The method of claim 1, wherein the normal blood pressure range comprises a systolic blood pressure no greater than 119 mmHg and a diastolic blood pressure no greater than 80 mmHg.

8. The method of claim 1, comprising triggering the alarm when the blood pressure is within the normal blood pressure range.

9. A monitoring system, comprising:
a sensor configured to sense patient physiological parameters; and
a monitor configured to receive an input from the sensor related to the patient physiological parameters, the monitor comprising:
one or more processors configured to:
determine a blood pressure baseline from the input; and
establish an alarm sensitivity based on the blood pressure baseline, wherein the alarm sensitivity comprises at least one tier corresponding to a normal blood pressure range and at least one tier corresponding to a high blood pressure range, and the alarm sensitivity is selected based on which blood pressure range encompasses the blood pressure baseline, wherein the alarm sensitivity relates to an acceptable percent shift of the blood pressure from the blood pressure baseline that if exceeded triggers an alarm, and the acceptable percent shift for the at least one tier corresponding to the normal blood pressure range is different from the acceptable percent shift of the at least one tier corresponding to the high blood pressure range.

10. The system of claim 9, wherein the sensor comprises a pulse oximeter sensor.

11. The system of claim 9, wherein the normal blood pressure range comprises a systolic blood pressure no greater than 119 mmHg and a diastolic blood pressure no greater than 80 mmHg.

12. The system of claim 9, wherein the one or more processors are configured to:
determine a blood pressure from the input; and
measure a percent shift of the blood pressure from the blood pressure baseline.

13. The system of claim 12, wherein the system is configured to trigger an alarm if the percent shift exceeds the established alarm sensitivity when the blood pressure is within the normal blood pressure range.

14. The system of claim 9, wherein the blood pressure baseline comprises a systolic blood pressure baseline and a diastolic blood pressure baseline, and wherein the alarm sensitivity comprises a first alarm sensitivity based on the systolic blood pressure baseline and a second alarm sensitivity based on the diastolic blood pressure baseline.

15. A monitor, comprising:
a connector port configured to receive input from a sensor related to patient physiological parameters; and
one or more processors configured to:
determine a systolic blood pressure baseline and a diastolic blood pressure baseline from the input; and
establish a first alarm sensitivity for systolic blood pressure based on the systolic blood pressure baseline and a second alarm sensitivity for diastolic blood pressure based on the diastolic blood pressure baseline, wherein the first and the second alarm sensitivities comprise multiple tiers, wherein the first alarm sensitivity relates to an acceptable percent shift of the systolic blood pressure from the systolic blood pressure baseline that if exceeded triggers an alarm and the second alarm sensitivity relates to an acceptable percent shift of the diastolic blood pressure from the diastolic blood pressure baseline that if exceeded triggers an alarm, and the acceptable percent shift for the at least one of the multiple tiers is different from the acceptable percent shift of at least one other tier of the multiple tiers.

16. The monitor of claim 15, wherein the first alarm sensitivity comprises at least one tier corresponding to a normal systolic blood pressure and at least one tier corresponding to a high systolic blood pressure, and the second alarm sensitivity comprises at least one tier corresponding to a normal diastolic blood pressure and at least one tier corresponding to a high diastolic blood pressure.

17. The monitor of claim 16, wherein the first alarm sensitivity is selected based on which systolic blood pressure range encompasses the systolic blood pressure baseline and the second alarm sensitivity is selected based on which diastolic blood pressure range encompasses the diastolic blood pressure baseline.

18. The monitor of claim 16, wherein the monitor is configured to trigger an alarm if a measured percent shift of the systolic blood pressure exceeds the first alarm sensitivity when the systolic blood pressure is within the normal systolic blood pressure rate range.

19. The monitor of 15, wherein the one or more microprocessors are configured to:
   determine a systolic blood pressure and a diastolic blood pressure from the input; and
   measure a percent shift of the systolic blood pressure from the systolic blood pressure baseline and of the diastolic pressure from the diastolic blood pressure baseline.

20. The monitor of claim 19, comprising a display, wherein the display is configured to display one or more graphical indicators comprising the systolic blood pressure, the diastolic blood pressure, the systolic blood pressure baseline, the diastolic blood pressure baseline, the first alarm sensitivity, the second alarm sensitivity, the percent shift of the systolic blood pressure from the systolic blood pressure baseline, the percent shift of the diastolic blood pressure from the diastolic blood pressure baseline, or any combination thereof.

* * * * *